United States Patent
Simandan et al.

(10) Patent No.: US 7,151,188 B1
(45) Date of Patent: Dec. 19, 2006

(54) PROCESS FOR THE PRODUCTION OF MERCAPTOALKYLALKOXYSILANES

(75) Inventors: Tiberiu L. Simandan, Marietta, OH (US); Michael R. Powell, New Martinsville, WV (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/280,698

(22) Filed: Nov. 16, 2005

(51) Int. Cl.
*C07F 7/08* (2006.01)

(52) U.S. Cl. ....................... 556/429; 556/427

(58) Field of Classification Search ................ 556/429, 556/427
See application file for complete search history.

(56) References Cited

U.S. PATENT DOCUMENTS

| | | | |
|---|---|---|---|
| 5,081,298 A | 1/1992 | Brunelle | |
| 5,116,975 A | 5/1992 | Brunelle | |
| 5,132,423 A | 7/1992 | Brunelle et al. | |
| 5,229,482 A | 7/1993 | Brunelle | |
| 5,830,974 A | 11/1998 | Schmidhauser et al. | |
| 5,905,150 A | 5/1999 | Simonian et al. | |
| 5,907,025 A | 5/1999 | Brunelle | |
| 5,908,915 A | 6/1999 | Brunelle | |
| 6,028,203 A | 2/2000 | Brunelle et al. | |
| 6,235,934 B1 | 5/2001 | Caringi et al. | |
| 6,570,038 B1 | 5/2003 | Caringi et al. | |
| 6,680,398 B1 | 1/2004 | Boswell et al. | |
| 6,706,897 B1 | 3/2004 | Brunelle et al. | |

*Primary Examiner*—Samuel Barts

(57) ABSTRACT

Mercaptoalkylalkoxysilane is obtained by reacting at least one sulfide of the general formula

MHS wherein M is an alkali metal or ammonium with a haloalkyl silane in an aqueous reaction medium in the presence of an acidic gas to maintain the pH of the reaction medium at or below about 10, and in the additional presence of alkylguanidinium salt phase transfer catalyst to provide mercaptoalkylalkoxysilane, the alkylguanidinium salt phase transfer catalyst being represented by the general formula:

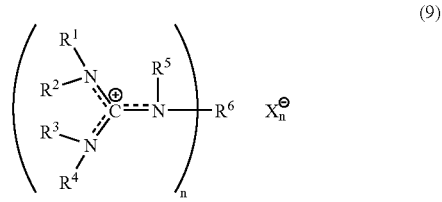

(9)

wherein each of $R^{1-5}$ is a primary alkyl radical and $R^6$ is a primary alkyl or bis(primary alkylene) radical, or at least one of the $R^1$–$R^2$, $R^3$–$R^4$ and $R^5$–$R^6$ combinations with the respective connecting nitrogen atom forms a heterocyclic radical; X is an anion; and n is 1 or 2.

26 Claims, No Drawings

PROCESS FOR THE PRODUCTION OF MERCAPTOALKYLALKOXYSILANES

This invention relates to the production of mercaptoalkylalkoxysilanes, compounds that are known to be useful as reactive coupling agents between rubber and silica fillers and as adhesion promoters between rubber and other materials such as glass and metals.

Sulfur-containing organosilicon compounds are difficult to produce by known synthetic processes due to the formation of undesirable co-products by various side reactions. These processes are deficient in terms of their yields, efficiency, and environmental acceptability. The demand for sulfur-containing organosilicon compounds continues to grow and consequently there is a need for a better, more efficient, less costly and more environmentally acceptable process for their production.

U.S. Pat. No. 6,680,398, the entire contents of which are incorporated by reference herein, describes a process for the production of mercaptoalkylalkoxysilanes in which an aqueous phase containing a sulfide is reacted with a haloalkyl silane in the presence of a pH adjusting agent providing a constant pH in the range of 4–9, and in the additional presence of phase transfer agent, thereby providing a reaction mixture containing mercaptoalkylalkoxysilanes and water soluble co-products.

SUMMARY OF THE INVENTION

In accordance with the present invention, there is provided a process for the production of mercaptoalkylalkoxysilane which comprises reacting at least one sulfide of the general formula

MHS wherein M is an alkali metal or ammonium group with a haloalkyl silane in an aqueous reaction medium in the presence of an acidic gas to maintain the pH of the reaction medium at or below about 10, and in the additional presence of alkylguanidinium salt phase transfer catalyst to provide mercaptoalkylalkoxysilane, the alkylguanidinium salt phase transfer catalyst being represented by the general formula:

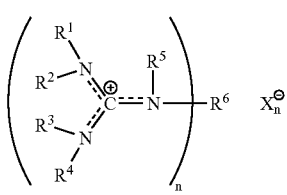

(1)

wherein each of $R^{1-5}$ is a primary alkyl radical and $R^6$ is a primary alkyl or bis(primary alkylene) radical, or at least one of the $R^1$–$R^2$, $R^3$–$R^4$ and $R^5$–$R^6$ combinations with the respective connecting nitrogen atom forms a heterocyclic radical; X is an anion; and n is 1 or 2.

The foregoing process for the production of mercaptoalkyl-alkoxysilane differs from that of U.S. Pat. No. 6,680,398 in using a phase transfer catalyst with unique properties that result in increased yield, higher purity and overall greater efficiency of the principal reaction under improved kinetic conditions.

DETAILED DESCRIPTION OF THE INVENTION

In the starting sulfide, MHS, M represents an alkali metal such as sodium, potassium, rubidium or cesium, or ammonium. Representative sulfides include NaHS, KHS and $NH_4HS$. In one embodiment, the sulfide is an aqueous solution containing from about 25 to about 72, and in another embodiment from about 40 to about 60, weight percent NaHS.

In a particular embodiment of the invention, the haloalkyl silane is represented by the general formula:

X—Alk—$SiR_m(OR)_{3-m}$ wherein X is halogen, i.e., fluorine, chlorine, bromine or iodine, and advantageously is chlorine; Alk is a divalent hydrocarbon group of from 1 to about 18 carbon atoms, and advantageously is from 2 to about 6 carbon atoms; R is a hydrocarbon group of from 1 to 12 carbon atoms, and advantageously is methyl or ethyl; and, m is 0, 1 or 2, and advantageously is 0.

Some specific haloalkyl silanes that can be used herein include 3-chloromethyl-1-triethoxysilane, 3-chloroethyl-1-triethoxysilane, 3-chloropropyl-1-triethoxysilane and 3-clorobutyl-1-triethoxysilane. Of these, 3-chloropropyl-1-triethoxysilane is particularly advantageous.

The molar ratio of sulfide to haloalkyl silane can, in general, vary from about 2:1 to about 1:1 and advantageously is from about 1.2:1 to about 1.1:1.

The pH of the reaction medium in a first embodiment is maintained at a level not exceeding about 10, in a second embodiment not exceeding about 9 and in a third embodiment not exceeding about 8.5, employing an acidic gas such as $H_2S$ (hydrogen sulfide), $SO_2$ (sulfur dioxide) or $CO_2$ (carbon dioxide). $H_2S$ has been found to provide generally good results when used at pressures of, e.g., from about 10 to about 100 psi in a first embodiment and from about 20 to about 60 psi in a second embodiment. In the specific case of $H_2S$ as the acidic gas and NaHS as the sulfide reactant, overhead pressures on the aforestated order maintain the NaHS in the aqueous phase thereby minimizing the formation of $Na_2S$. This is of importance since even at levels of as low as 0.5 weight percent, the presence of $Na_2S$ will cause the pH of the reaction medium to rise well above the maximum of 10.0 thereby leading to an increase in the coproduction of undesirable heavy products such as siloxanes. The use of $H_2S$ or other acidic gas in the process of this invention to control the pH of the reaction medium makes the use of buffers or other pH-adjusting compounds unnecessary.

The catalyst employed in the inventive process herein is a phase transfer alkylguanidinium salt. Useful alkylguanidinium salts, processes for their preparation and their uses as catalysts for other chemical syntheses are described in U.S. Pat. Nos. 5,081,298; 5,116,975; 5,132,423; 5,229,482; 5,830,974; 5,905,150; 5,907,025; 5,908,915; 6,028,203; 6,235,934; 6,570,038; and, 6,706,897, the entire contents of which are incorporated by reference herein.

The phase transfer alkylguanidinium salt employed in the process of this invention can be represented by the general formula:

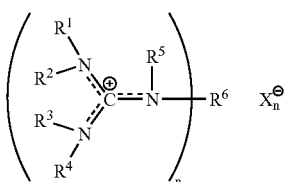

wherein each of $R^{1-5}$ is a primary alkyl radical and $R^6$ is a primary alkyl or bis(primary alkylene) radical, or at least one of the $R^1$–$R^2$, $R^3$–$R^4$ and $R^5$–$R^6$ combinations with the respective connecting nitrogen atom forms a heterocyclic radical; X is an anion; and n is 1 or 2.

Representative $R^{1-5}$ alkyl radicals include primary alkyl radicals, generally containing about 1–12 and especially 1–6 carbon atoms. $R^6$ is usually an alkyl radical of the same structure or a $C_2$–$C_{12}$ alkylene radical in which the terminal carbons are primary. In particular, $R^6$ is a $C_{2-6}$ alkyl or $C_{4-8}$ straight chain alkylene radical. Alternatively, any combination of $R^{1-6}$ radicals and the nitrogen atom(s) to which they are joined can form a heterocyclic radical such as a piperidino, pyrrolo or morpholino radical.

X can be any anion, strong acid such as fluoride, chloride, bromide, iodide, sulfate, bisulfate and methanesulfonate, carbonate, bicarbonate, phosphate, carboxylate, thiocarboxylate, and the like. Chloride and bromide ions are generally advantageous.

The value of n will be 1 or 2 depending on whether $R^6$ is alkyl or alkylene.

As indicated by the dotted bonds in the formula, the positive charge in the guanidinium salt is delocalized over one carbon and three nitrogen atoms. This is believed to contribute to the salts' stability under the relatively high temperature conditions encountered during use. As a result, decomposition of the alkylguanidinium salt does not occur or occurs only to a very minor extent under the conditions of the process of the invention. The advantages of employing the foregoing alkylguanidinium salt in the process of the invention include suppression of by-product formation and potential for continued use via recycle.

The alkylguanidinium phase transfer catalyst can be added to the reaction medium as salts, or as concentrated or dilute solutions in water and/or other suitable solvents, such as alcohols. The quantity of catalyst used will depend on the desired rate of reaction and the level of side products which can be tolerated, among other factors. Suitable concentrations include a concentration of from about 1 ppm (part per million by weight) to about 3 percent by weight. Specific embodiments of concentrations include from about 10 ppm to about 1 weight percent and advantageously from about 50 ppm to about 0.5 weight percent. Quantities below 1 ppm of phase transfer catalyst might be much the same as those obtained without the use of a phase transfer catalyst.

Specific examples of suitable alkylguanidinium phase transfer catalysts for use herein include those whose structures and chemical names appear below:

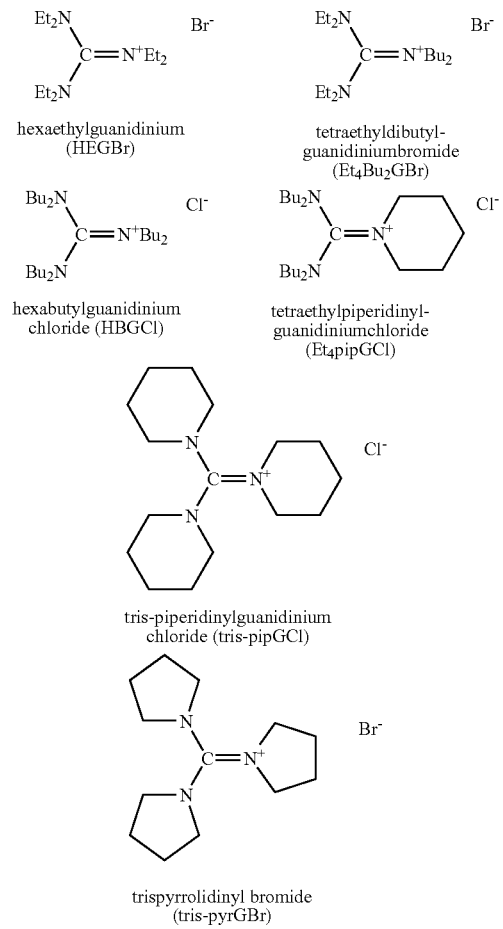

The process of the invention is carried out in an aqueous/organic phase containing the sulfide, haloalkyl silane, acidic gas and alkylguanidinium phase transfer catalyst. The amount of water used in preparing the aqueous reaction medium can be added directly, or it can be present indirectly, i.e., as the water present in the sulfide reactant. In any case, the total amount of water for purposes of the invention will include all water added directly or indirectly. Accordingly, the total amount of water employed in providing the aqueous phase can vary from about 2.5 to about 70 weight percent, and in another embodiment, from about 20 to about 40 weight percent, of the total reaction medium.

Example 1

The reaction apparatus included a 1000 mL 45 psig-rated pressure glassware with "Hi-Pressure" Teflon fittings, mechanical stirrer, temperature control, heating mantle, and a source of $H_2S$ gas (lecture bottles from Sigma-Aldrich, Milwaukee, Wis.).

The reactor was charged with 198 grams 45% aqueous NaSH solution (89.1 grams pure NaSH, 1.59 mmoles) and 114.1 grams 35% hexaethylguanidinium chloride (HEGCl) aqueous solution (40 grams pure, 0.15 mmoles), under stirring. Also, 360.4 grams (1.5 mmoles) of chloropropyltriethoxysilane (CPTES) were batch charged to the reactor. From a lecture bottle, $H_2S$ pressure was generated in the reactor to about 17 psi. The system was heated to 98° C., while the pressure increased to about 20 psi and maintained under these condition for about 6 hours. After cooling to room temperature, the H$_2$S was vented off and an additional 275 grams of water were charged to the reactor. After stopping the agitation and phase separation, the top layer (346.2 grams) was removed and analyzed by gas chromatography (GC), revealing the following composition: 1.06 weight % ethanol, 19.9 weight % unreacted CPTES, 73.4 weight % mercaptopropyltriethoxysilane (MPTES), and 4.8 weight % heavies. The molar yield of MPTES was 74% based on CPTES.

Comparative Example 1

This example illustrates the preparation of MPTES in the absence of alkylguanidinium salt phase transfer catalyst.

Employing the apparatus of Example 1, MPTES was prepared by continuous addition of CPTES to the reaction mixture at 75° C. over 3 hours. The H$_2$S pressure was maintained at about 17.5 psi. After 7 hours overall, the organic phase contained 70.2 weight % unreacted CPTES and 29.3 weight % MPTES.

Comparative Example 2

This example illustrates the preparation of MPTES employing tetrabutylammonium bromide (TBAB) phase transfer catalyst as described in U.S. Pat. No. 6,680,398.

Employing the apparatus of Example 1, 263.97 g NaSH (2.119 moles/1.100 equiv.), 488.04 CPTES (1.927 moles) and 95.22 g TBAB (50 weight percent aqueous solution) were charged to the reactor which was then heated to 98° C. under a pressure of approximately 21 psig H$_2$S and maintained under these conditions for 8 hours. To the reaction mixture were then added 414 g water followed by separation of the reaction mixture into a bottom layer (769.7 g) and a top layer (358.8 g). Analysis of the crude top layer by GC revealed the following composition: 2.9 weight % ethanol, 2.33 weight % CPTES, 84.09 weight % MPTES and 5.56 weight % heavies. The molar yield of MPTES was 66% based on CPTES.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

What is claimed is:

1. A process for the production of mercaptoalkylalkoxysilane which comprises reacting at least one sulfide of the general formula

MHS wherein M is an alkali metal or ammonium with a haloalkyl silane in an aqueous reaction medium in the presence of an acidic gas to maintain the pH of the reaction medium at or below about 10, and in the additional presence of alkylguanidinium salt phase transfer catalyst to provide mercaptoalkylalkoxysilane, the alkylguanidinium salt phase transfer catalyst being represented by the general formula:

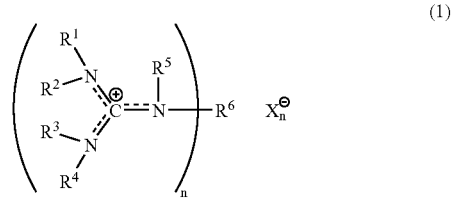

wherein each of $R^{1-5}$ is a primary alkyl radical and $R^6$ is a primary alkyl or bis(primary alkylene) radical, or at least one of the $R^1$–$R^2$, $R^3$–$R^4$ and $R^5$–$R^6$ combinations with the respective connecting nitrogen atom forms a heterocyclic radical; X is an anion; and n is 1 or 2.

2. The process of claim 1 wherein the sulfide is NaHS.

3. The process of claim 1 wherein the haloalkyl silane is represented by the formula:

X—Alk—SiR$_m$(OR)$_{3-m}$ wherein X is halogen; Alk is a divalent hydrocarbon group of from 1 to about 18 carbon atoms; R is a hydrocarbon group of from 1 to 12 carbon atoms; and m is 0, 1 or 2.

4. The process of claim 3 wherein X is chlorine, Alk is from 2 to about 6 carbon atoms, R is methyl or ethyl and m is 0.

5. The process of claim 1 wherein the haloalkyl silane is 3-chloropropyl-1-triethoxysilane.

6. The process of claim 2 wherein the haloalkyl silane is 3-chloropropyl-1-triethoxysilane.

7. The process of claim 1 wherein the acidic gas is H$_2$S.

8. The process of claim 7 wherein the pH is maintained at a level not exceeding about 9.

9. The process of claim 7 wherein the pH is maintained at a level not exceeding about 8.5.

10. The process of claim 2 wherein the reaction medium is maintained at a pressure of from about 10 to about 100 psi with H$_2$S and the pH of the reaction medium is maintained at a level not exceeding about 9.

11. The process of claim 2 wherein the reaction medium is maintained at a pressure of from about 20 to about 60 psi with H$_2$S and the pH of the reaction medium is maintained at a level not exceeding about 8.5.

12. The process of claim 1 wherein the reaction medium contains from about 2.5 to about 85 weight percent water.

13. The process of claim 1 wherein the reaction medium contains from about 20 to about 40 weight percent water.

14. The process of claim 1 wherein the molar ratio of sulfide to haloalkyl silane is from about 2:1 to about 1:1.

15. The process of claim 1 wherein the molar ratio of sulfide to haloalkyl silane is from about 1.2:1 to about 1.1–1.

16. The process of claim 1 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

17. The process of claim 2 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

18. The process of claim 3 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

19. The process of claim 4 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

20. The process of claim 5 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

21. The process of claim 6 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

22. The process of claim 7 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

23. The process of claim 8 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

24. The process of claim 10 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

25. The process of claim 12 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

26. The process of claim 14 wherein the alkylguanidinium salt is at least one member selected from the group consisting of hexaethylguanidinium bromide, tetramethyldibutylguanidinium bromide, hexabutylguanidinium chloride, tetraethylpiperidinylguanidinium chloride, tris-piperidinylguanidinium chloride, trispyrrolidinyl bromide and mixtures thereof.

* * * * *